US008268211B2

(12) United States Patent
Sato

(10) Patent No.: US 8,268,211 B2
(45) Date of Patent: Sep. 18, 2012

(54) METHOD AND APPARATUS FOR MAKING BODILY FLUID ABSORBENT PAD

(75) Inventor: Hidenori Sato, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 194 days.

(21) Appl. No.: 12/524,085

(22) PCT Filed: Jul. 21, 2009

(86) PCT No.: PCT/JP2009/063021
§ 371 (c)(1),
(2), (4) Date: Oct. 2, 2009

(87) PCT Pub. No.: WO2011/001543
PCT Pub. Date: Jan. 6, 2011

(65) Prior Publication Data
US 2011/0154964 A1 Jun. 30, 2011

(30) Foreign Application Priority Data
Jun. 30, 2009 (JP) ................................. 2009-156295

(51) Int. Cl.
*B28B 11/16* (2006.01)

(52) U.S. Cl. ...................................................... 264/146

(58) Field of Classification Search ................... 264/146
See application file for complete search history.

(56) References Cited

U.S. PATENT DOCUMENTS

| 4,862,574 A | 9/1989 | Seidy | |
|---|---|---|---|
| 2003/0087056 A1* | 5/2003 | Ducker et al. | 428/57 |
| 2006/0247590 A1* | 11/2006 | Ito et al. | 604/379 |

FOREIGN PATENT DOCUMENTS

| JP | 2005-218648 A | 8/2005 |
|---|---|---|
| JP | 2006-020977 A | 1/2006 |
| JP | 2006-305243 A | 11/2006 |
| WO | 97/27032 A1 | 7/1997 |

OTHER PUBLICATIONS

PCT/JP2009/063021 International Search Report.

* cited by examiner

*Primary Examiner* — Larry Thrower
(74) *Attorney, Agent, or Firm* — Lowe, Hauptman, Ham & Berner, LLP

(57) ABSTRACT

In making bodily fluid absorbent pads quantity of scrapped material is reduced. A bodily fluid absorbent pad (liner) 10 has a shape symmetric in a longitudinal direction P as well as in a transverse direction Q. A dimension of the pad 10 in the transverse direction Q is larger in opposite end regions 31, 32 than in an intermediate region 33. The pad 10 is formed along opposite side edges 11a, 11b with first and second compressed lines 21, 22. Paired compression rolls 302 are used to form the first and second compressed lines 21, 22, and at least one roll constituting the paired compression rolls 302 is formed on a peripheral surface thereof with compressing units projecting from the peripheral surface. The compressing units are arranged in a circumferential direction to form one row and at least one additional row, which is adjacent to the one row in an axial direction of the roll. In each pair of the adjacent rows, there is an offset between the compressing unit in the one row and the compressing units in the other row in the circumferential direction.

16 Claims, 11 Drawing Sheets

METHOD AND APPARATUS FOR MAKING BODILY FLUID ABSORBENT PAD

RELATED APPLICATIONS

The present application is based on, and claims priority from, International Application PCT/JP2009/63021, filed Jul. 21, 2009 and Japan Application Number 2009-156295, filed Jun. 30, 2009, the disclosures of which are hereby incorporated by reference herein in their entirety.

TECHNICAL FIELD

The present invention relates to method and apparatus to make a bodily fluid absorbent pad suitable to use in a form of various articles such as panty liner and sanitary napkin.

RELATED ART

A bodily fluid absorbent pad such as panty liner is well known. Such pad shaped to be symmetric with respect to a longitudinal center line as well as a transverse center line is also well known.

For example, an absorbent article disclosed in PATENT DOCUMENT 1 is shaped to be symmetric with respect to a longitudinal center line as well as a transverse center line and comprises a pair of absorbent article components being same in shape as well as in size put flat together in a thickness direction and partially compressed under heating so as to be detachably attached to each other along compressed lines. When the upper absorbent article component has been contacted with a wearer's skin and soiled with bodily fluids, the upper absorbent article component may be peeled off from the lower absorbent article component and in turn, this lower one may be contacted with the wearer' skin. Each of the absorbent article has a dimension in the transverse direction or the width of the article is larger in end regions opposite in the longitudinal direction than in an intermediate region defined between the end regions. The compressed lines along which the upper and lower absorbent article components are attached together extend in the longitudinal direction along the side edges of the article.

CITED REFERENCES

Patent Document

Patent Document 1: JP 2006-305243 A

SUMMARY OF THE INVENTION

Problem to be Solved by the Invention

In a bodily fluid absorbent web from which the absorbent article components used for the absorbent article disclosed in PATENT DOCUMENT 1 are cut out, the individual absorbent article components line up sideways and each pair of the adjacent absorbent article components leaves therebetween a relatively large space since the width of the absorbent article component is larger in the opposite end regions than in the intermediate region. As a consequence, in the step of cutting out the individual absorbent article components inevitably generates scrap in large quantity. Furthermore, when a fibrous web having a thickness in a range of 0.5 to 2 mm is used as the web formed with compressed lines, the depth and the appearance of the compressed lines might become uneven depending on the individual absorbent article components.

The present invention intends to solve such problems occurring in the course of making the bodily fluid absorbent pad.

Measure to Solve the Problem

The present invention to achieve the object set forth above include a first aspect relating to a method for making a bodily fluid absorbent pad and a second aspect relating to an apparatus for making such bodily fluid absorbent pad.

The object set forth above is achieved, according to the present invention on the first aspect, by an improvement in the method for making a bodily fluid absorbent pad, the pad having a longitudinal direction, a transverse direction and a thickness direction being orthogonal one to another and shaped so as to be relatively long in the longitudinal direction, wherein the pad having a skin-contact surface and a skin-noncontact surface being an opposite surface of the skin-contact surface as viewed in the thickness direction, and a dimension in the transverse direction being larger in first and second end regions opposite to each other in the longitudinal direction than in an intermediate region extending between the first and second end regions, and wherein the pad is formed on the skin-contact surface with compressed lines extending in the longitudinal direction inside respective side edges extending in parallel with each other in the longitudinal direction thereof.

The improvement according to the present invention on the first aspect thereof is characterized by comprising steps as follow: feeding a bodily fluid absorbent web in a machine direction through paired compression rolls to partially compress the bodily fluid absorbent web and thereby to form the compressed lines comprising first and second compressed segments in the first and second end regions, respectively, and third compressed segments extending in the intermediate region, wherein compressing units for forming the compressed lines are provided on and projecting from a peripheral surface of at least one roll constituting the paired compression rolls and the compressing units are adapted to form one row extending in a circumferential direction and also wherein at least one additional row of the compressing units which is adjacent to and in parallel with the one row is provided in an axial direction of the one roll; and wherein there is an offset in the circumferential direction between the compressing units in the one row and the compressing unit in the one additional row so that the first and second compressed segments formed by the compressing units in the one row are lateral to the third compressed segment formed by the compressing unit in the one additional row, respectively; and making two or more rows of the bodily fluid absorbent pads from the bodily fluid absorbent web.

According to one preferred embodiment of the present invention on the first aspect thereof, the method further includes a step of feeding a bodily fluid absorbent web through paired cutter rolls provided on downstream of the paired compression rolls in the machine direction to cut out the bodily fluid absorbent pads from the bodily fluid absorbent web having passed through the paired compression rolls wherein knife edges are provided on a peripheral surface of one cutter roll constituting the paired cutter rolls and arranged in an arrangement corresponding to an arrangement of the compressing units provided on said one compression roll constituting the paired compression rolls in the circumferential direction as well as in the axial direction.

According to another preferred embodiment of the present invention on the first aspect thereof, the method further includes, between the step of feeding the bodily fluid absorbent web through the paired compression rolls and the step of feeding the bodily fluid absorbent web through the paired cutter rolls, a step of permanently attaching bodily fluid impervious web defining the skin-noncontact surface in the bodily fluid absorbent pad to the bodily fluid absorbent web.

According to still another preferred embodiment of the present invention on the first aspect thereof, the method further includes before the step of feeding the bodily fluid absorbent web through the paired compression rolls, a step of placing a second bodily fluid absorbent web upon a skin-contact surface of the bodily fluid absorbent web destined to be the skin-contact surface of the bodily fluid absorbent pad and then seperably attaching the bodily fluid absorbent web and the second bodily fluid absorbent web to each other to make bodily fluid absorbent composite pads comprising the bodily fluid absorbent pads.

According to yet another preferred embodiment of the present invention on the first aspect thereof, the method further characterized in that at least one compression roll constituting the paired compression rolls is formed so as to receive a rod heater inserted thereinto wherein said rod heater is designed so that a watt density is higher at end regions thereof opposite to each other in the axial direction than in an intermediate region thereof extending between the end regions thereof.

The object set forth above is achieved, according to the present invention on the second aspect thereof, by improvement in an apparatus for implementation of the method for making the bodily fluid absorbent pad.

The improvement in the apparatus according to the present invention on the second aspect thereof is characterized in the following features: one compression roll constituting the paired compression rolls adapted to compress the bodily fluid absorbent web has the compressing units projecting from the peripheral surface thereof and arranged in one row extending in a circumferential direction and also arranged in at least one additional row of said compressing units adjacent in an axial direction and extending in parallel with the one row of compressing units and there is an offset in the circumferential direction between the compressing unit in the one row and the compressing unit in the one additional row; and a third region in the one row adapted to form the third compressed segments are lateral to first and second regions in the additional row adapted to form the first and second compressed segments and opposed to each other in the circumferential direction.

According to one preferred embodiment according to the present invention on the second aspect thereof, paired cutter rolls used to cut out the bodily fluid absorbent pads from the bodily fluid absorbent web is provided on downstream of the paired compression rolls in the machine direction and one cutter roll constituting the paired cutter rolls is provided on a peripheral surface thereof with knife edges in an arrangement corresponding to an arrangement of the compressing units on the one compression roll constituting the paired compression rolls in the circumferential direction as well as in the axial direction wherein the knife edges project from the peripheral surface of the one cutter roll constituting the paired cutter rolls and the other cutter roll of the paired cutter rolls has a smooth peripheral surface.

According to another preferred embodiment according to the present invention on the second aspect thereof, compressing units are provided on and projected from the peripheral surface of the other one compression roll constituting the paired compression rolls and cooperate with the compressing units on the one compression roll constituting the paired compression rolls to compress the bodily fluid absorbent web.

According to still another preferred embodiment according to the present invention on the second aspect thereof, the peripheral surface of the one compression roll constituting the paired compression rolls includes regions each surrounded by the third region and the first and second regions opposed to each other in the circumferential direction, and each of these surrounded regions is formed with a small projection adapted to form an additional compressed line appearing in the bodily fluid absorbent web but not in the bodily fluid absorbent pad.

Effect of the Invention

The method and the apparatus according to the present invention for making the disposable bodily fluid absorbent pad provide advantageous effect as follows. In the process of continuously making the pads, the compressing units formed on the paired compression rolls adapted to act on the web running in the machine direction are set in array so as to form two or more rows in the machine direction and, in each pair of the rows being adjacent in the cross direction, the regions of the compressing units in one row adapted to form in the end regions of the pad with the compressed end segments are lateral to the regions of the compressing units in the adjacent row adapted to form in the intermediate region of the pad with the compressed intermediate segments. The individual pads can be cut out from such web with scrap as reduced as possible. Furthermore, there is no risk that the area over which the paired compression rolls used to form the pads with the compressed lines come in contact with the web might be abruptly changed and thereby might damage the web and/or the paired compression rolls.

Figure 1:
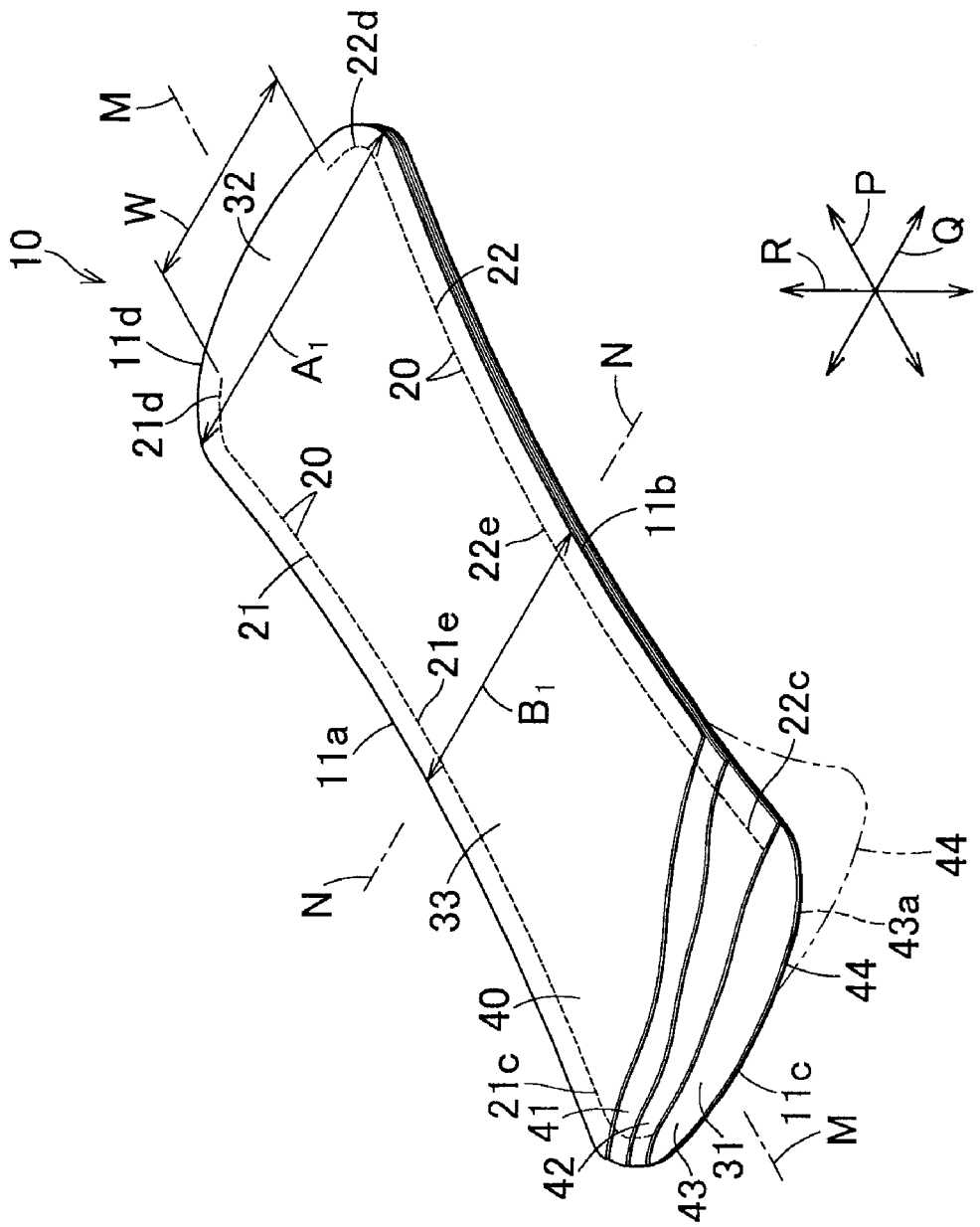
FIG. 1 is a partially cutaway perspective view of the liner.

IDENTIFICATION OF REFERENCE NUMERALS USED IN THE DRAWINGS 10 pad (liner)
11 first pad (upper liner)
11a side edge
11b side edge
11c end edge
11d end edge 20 small compressed spot(s)
21 compressed line (first compressed line)
21c first compressed end segment
21d second compressed end segment
21e third compressed segment
22 compressed line (second compressed line)
22c first compressed end segment
22d second compressed end segment
22e third compressed segment
31 first end region
32 second end region
33 intermediate region
43a skin-noncontact surface
113 second bodily fluid absorbent web
115 bodily fluid absorbent web (second laminated web)
116 first composite web
117 second composite web
127 bodily fluid impervious web
302 paired compression rolls
302a first compression roll
302b second compression roll
330 cutter roll pair
331a first cutter roll
331b second cutter roll
341 third region
342 third region
343 first region
344 second region
351 compressing unit (projection)
352 first projection (small projection)
360 surrounded region
361 second compressing unit (anvil-mode projection)
362 second projection (anvil-mode projection)
380 heater
381 knife edge
390 composite pad

DETAILED DESCRIPTION OF THE PREFERRED EMBODIMENTS

The present invention will be described more in details in reference to the accompanying drawings on the basis of the panty liner as a typical embodiment of the bodily fluid absorbent pad made by the method and the apparatus according to the present invention.

FIG. 1 is a partially cutaway perspective view of a panty liner 10. The panty liner 10 has a longitudinal direction P, a transverse direction Q and a thickness direction R which are orthogonal one to another, and is symmetrically shaped with respect to the center line M bisecting the dimension thereof in the transverse direction Q as well as the center line N bisecting the dimension thereof in the longitudinal direction P. The liner 10 is contoured by a pair of side edges 11a, 11b extending in parallel with each other in the longitudinal direction P and a pair of end edges 11c, 11d extending in the transverse direction Q wherein these end edges 11c, 11d are connected to the side edges 11a, 11b, respectively. The liner 10 is shaped so as to be relatively long in the longitudinal direction P. In the transverse direction Q, the liner 10 is relatively wide in opposite end regions 31, 32 and zones having the maximum width $A_1$ are included in these end regions 31, 32. In the longitudinal direction P, an intermediate region 33 extending between the end regions 31, 32 is narrower than the end regions 31, 32 and includes a zone having the minimum width $B_1$. In the end regions 31, 32, the end edges 11c, 11d describe curved lines which are convex outwardly of the liner 10 and, in the intermediate region 33, the side edges 11a, 11b describe curved lines which are convex inwardly of the liner 10.

The liner 10 further comprises a top-sheet 40, first and second intermediate sheets 41, 42, a back-sheet 43 and a release paper 44 so that pressure-sensitive adhesive (not shown) coated on the back-sheet 43 can be exposed as the release paper 44 is peeled off from the back-sheet 43. The liner 10 is formed along the side edge 11a thereof with a first compressed line 21 and along the side edge 11b thereof with a second compressed line 22 which is symmetric with the first compressed line 21 in the transverse direction Q. Both the first compressed line 21 and the second compressed line 22 are assemblies comprising a plurality of small compressed spots 20 arranged in the longitudinal direction P so as to be spaced one from another and to define respective queues extending into the opposite end regions 31, 32 of the liner 10. In the end regions 31, 32, the first compressed line 21 and the second compressed line 22 are spaced from each other by a dimension W as measured in the transverse direction Q. The first compressed line 21 includes compressed end segments 21c, 21d in the respective end regions 31, 32, and a compressed intermediate segment 21e in the intermediate region 33 between the compressed end segments 21c, 21d. Similarly, the second compressed line 22 includes compressed end segments 22c, 22d and a compressed intermediate segment 22e. As will be described later more in detail, the top-sheet 40 and the first and second intermediate sheets 41, 42 put flat together to form a bodily fluid absorbent structure of the liner 10 are locally compressed by the paired compression rolls with or without heating to obtain the small compressed spots 20. In each of these small compressed spots 20, materials respectively forming these sheets 40, 41, 42 are mechanically entangled one with another to prevent peel-off of these sheets 40, 41, 42 occurring in the vicinity of the side edges 11a, 11b and, at the same time, to provide the liner 10 with a decorative effect.

Such liner 10 has basically a laminated structure comprising the bodily fluid pervious top-sheet 40 made of non-woven fabric containing thermoplastic synthetic fiber or perforated plastic film, the first and second intermediate sheets 41, 42 which are bodily fluid absorbent and made of non-woven fabric containing thermoplastic synthetic fiber and the back-sheet 43 made of plastic film or non-woven containing thermoplastic synthetic fiber. These sheets placed one upon another are permanently attached together by hot melt adhesive (not shown) so that the top-sheet 40 cooperates with the first and second intermediate sheets 41, 42 to form a layer adapted to absorb and to retain bodily fluids while the back-sheet 43 forms a bodily fluid impervious layer adapted to prevent bodily fluids from transferring to the wearer's garment. The thermoplastic synthetic fiber contained in the bodily fluid absorbing/retaining layer is preferably modified to become hydrophilic. This layer may contain liquid-absorbent fiber such as pulp fiber. The top-sheet 40 defines the skin-contact surface of the liner 10 and the back-sheet 43 defines the skin-noncontact surface of the liner 10 opposed to the skin-contact surface, i.e., the garment-contact surface 43a adapted to be put in contact with the wearer's garment (not shown). This garment-contact surface 43a is coated with pressure-sensitive adhesive (not shown) which is, in turn, protectively covered with a separator 44.

The exemplarily illustrated liner 10 is shaped to be symmetric with respect to the center line M as well as the center line N so that the liner 10 can be properly put on the wearer's body whether the end 11c is in front or the end 11d is in front. However, it is not essential for the liner 10 to be symmetric with respect to the center line N and it is possible to shape the liner 10 asymmetrically with respect to the center line N depending on the intended purpose.

Figure 2:
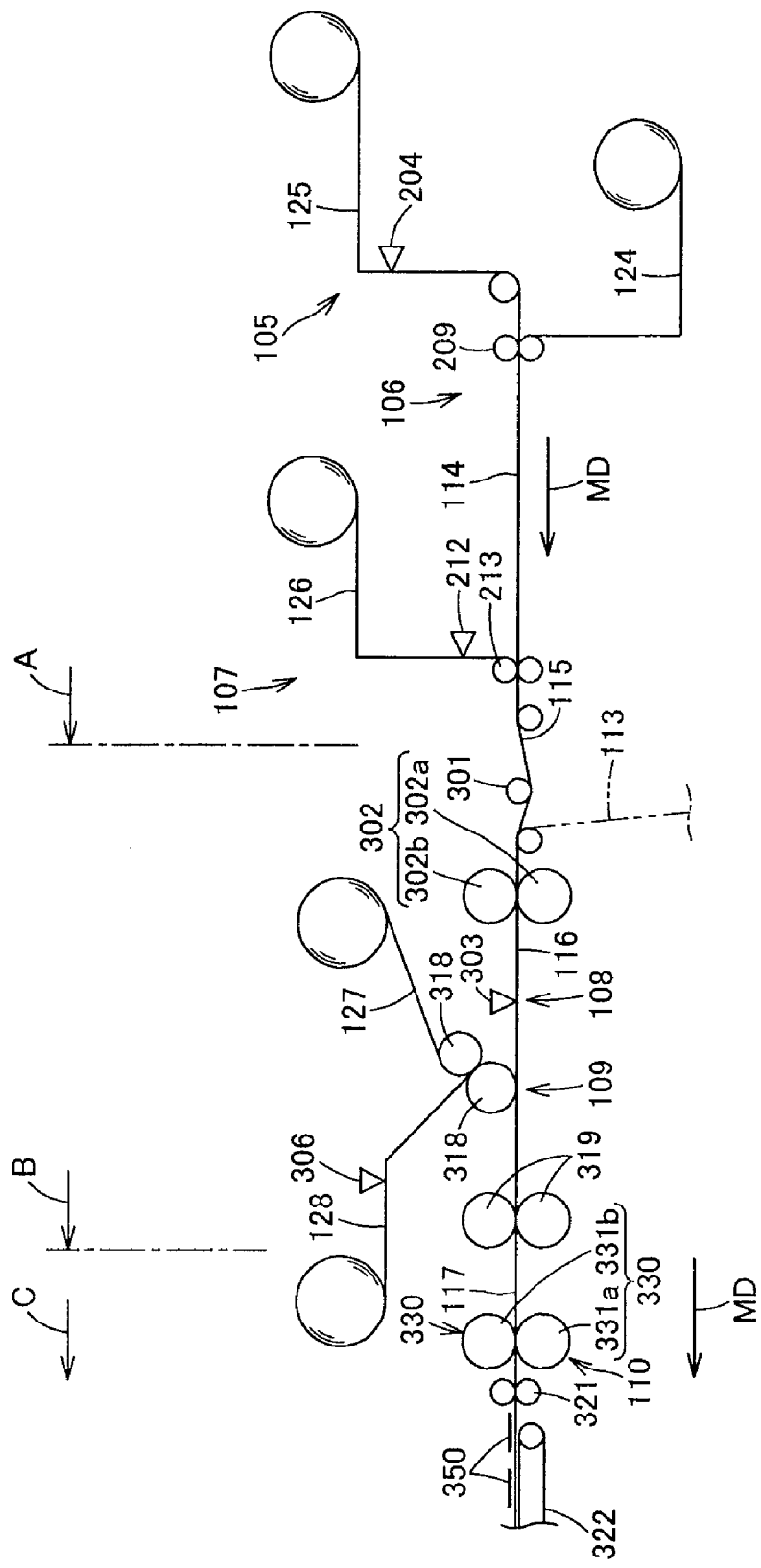
FIG. 2 is a diagram schematically illustrating a process of making the liner.

FIG. 2 exemplarily and schematically illustrates a process of making the liner 10. The process comprises a first section A to obtain the bodily fluid absorbent layer of the liner 10, a second section B to obtain the bodily fluid impervious layer after the bodily fluid absorbent layer has been formed with the first and second compressed lines 21, 22, and a third section C following the second section B.

The first section A includes a first step 105 through a third step 107. Specifically, in the first step 105, a first web 124 from which the top-sheet 40 will be obtained and a second web 125 from which the first intermediate sheet 41 will be obtained are fed from the right hand as viewed in FIG. 2 in a machine direction MD. Also in the first step 105, a coater 204 is used to coat one surface of the second web 125 with hot melt adhesive (not shown).

In the second step 106, the first and second webs 124, 125 are fed to paired nip rolls 209 and attached to each other by hot melt adhesive coated on the second web 125 to obtain a first laminated web 114.

In the third step 107, a third web 126 from which the second intermediate sheet 42 will be obtained is fed in the machine direction MD and, in the course of feeding this third web 126, a coater 212 is used to coat one surface of the third web 126 with hot melt adhesive (not shown). Also in the third step 107, paired nip rolls 213 rotating in the machine direction MD is used to attach the first laminated web 114 to the third web 126 having been coated with hot melt adhesive and thereby to obtain a second laminated web 115.

The second section B includes a fourth step 108 and a fifth step 110. Specifically, in the fourth step 108, the second laminated web 115 being kept by a tension controller 301 under a predetermined tension in the machine direction MD is fed to paired compression rolls 302 consisting of a first roll 302a and a second roll 302b. The first roll 302a is formed on its peripheral surface with projections 351 (See FIGS. 3 and 4) corresponding to the respective small compressed spots 20 (See FIG. 1) while the second roll 302b is formed on its peripheral surface with anvil-mode projections 361 (See FIGS. 5 and 6) opposed to the associated projections 351. Passing through the paired compression rolls 302, regions of the second laminated web 115 in which the first compressed line 21 and the second compressed line 22 will be formed are compressed so that at least the first, second and third webs 124, 125, 126 constituting the second laminated web 115 may be mechanically entangled together. In this way, a first composite web 116 is obtained. To enhance a compressing effect, it is also possible to use the first and second compression rolls 302a, 302b under heating. Also in the fourth step 108, a coater 303 is used to coat the third web 126 constituting the first composite web 116 with hot melt adhesive (not shown).

In the fifth step 109, a fourth web 127, a bodily fluid impervious web from which the back-sheet 43 of the liner 10 will be obtained and a fifth web 128 from which the separator 47 of the liner 10 will be obtained are fed in the machine direction MD. A coater 306 is used to coat one surface of the fifth web 128 with hot melt adhesive (not shown). The fourth web 127 and the fifth web 128 are fed to paired nip rolls 318 to attach these fourth and fifth webs 127, 128 to each other by adhesive previously coated on the fifth web 128. Then the fourth web 127 is put flat upon the third web 126 of the first composite web 116 previously coated with adhesive by the coater 303. The fourth web 127, the fifth web 128 and the first composite web 116 are fed so as to pass through paired nip rolls 319 and to be attached together. In this way, a second composite web 117 is obtained.

In the sixth step 110 of the third section C, the second composite web 117 is continuously fed to paired cutter rolls 330 consisting of two rolls 331a, 331b rotating in the machine direction MD and thereby individual composites 350, i.e., the individual liners 10 as shown by FIG. 1 are successively cut out from the web 117.

In downstream steps subsequent to the sixth step 110, appropriate means such as paired conveyer rolls 321 or an endless belt 322 is used to convey the individual composites 350 in the machine direction MD and, in the course of conveying, these composites 350 are successively wrapped, for example, by the plastic film to obtain envelopes each containing therein the liner 10.

Figure 3:
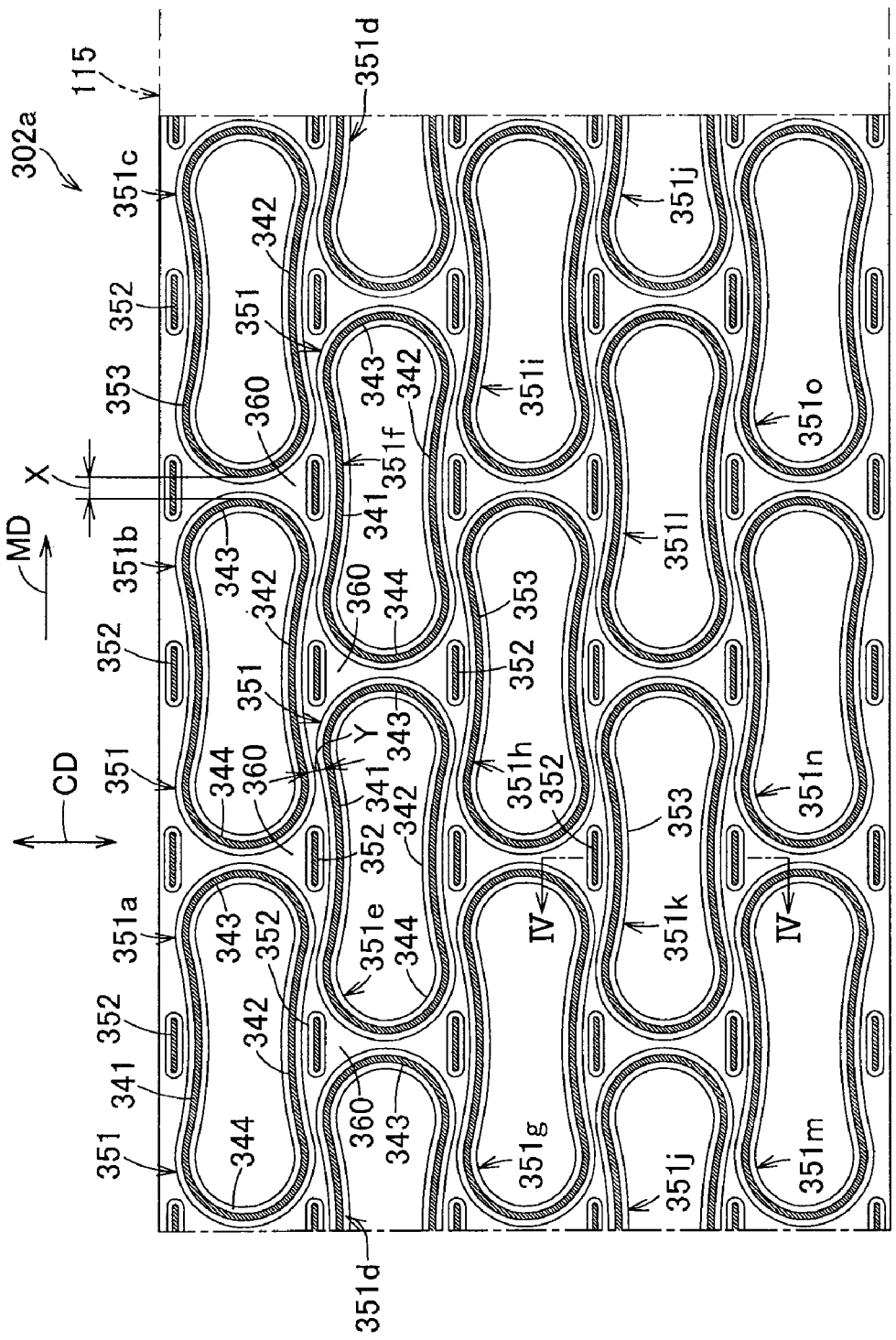
FIG. 3 illustrates the peripheral surface of the first roll constituting the paired compression rolls as has been flatly developed.
Figure 4:
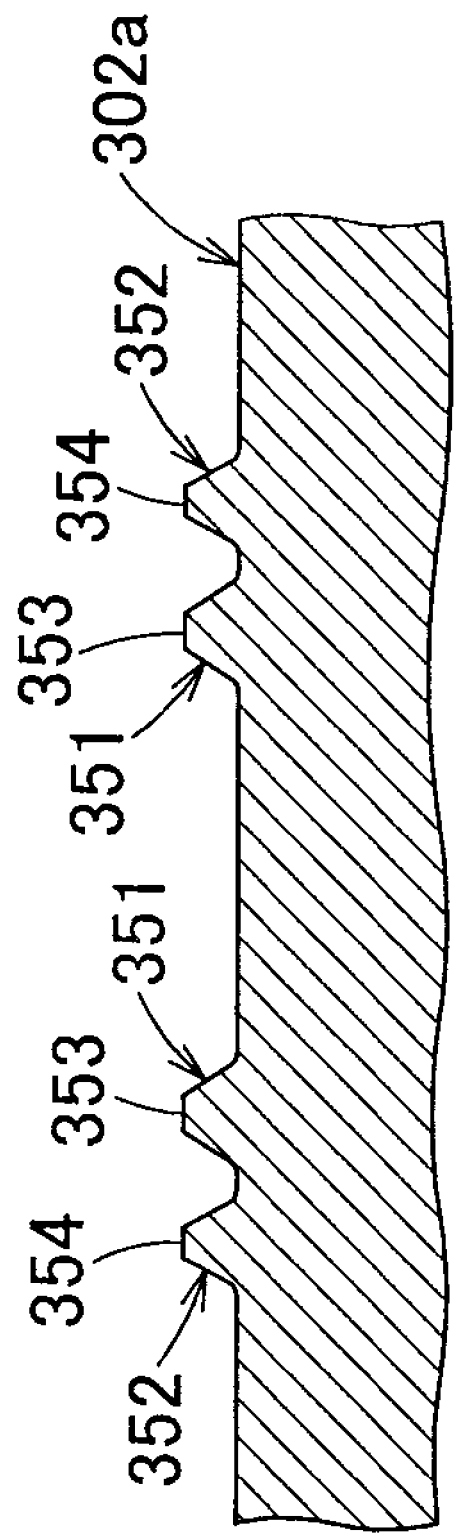
FIG. 4 is a sectional view taken along a line IV-IV in FIG. 3.

Referring to FIGS. 3 and 4, FIG. 3 illustrates the peripheral surface of the first roll 302a constituting the paired compression rolls 302 used in the process illustrated by FIG. 2 as has been flatly developed and FIG. 4 is a sectional view taken along a line IV-IV in FIG. 3. The first roll 302a depicted in FIG. 3 is formed on the peripheral surface thereof with, in addition to a plurality of loop-shaped projections 351 adapted to form the first compressed line 21 and the second compressed line 22, a plurality of small projections 352 extending in the machine direction MD. These projections 351 and the small projections 352 have profiles as illustrated by FIG. 4. The projections 351 and the small projections 352 shaded in FIG. 3 for convenience of illustration respectively have top surfaces 353, 354 of which at least the top surfaces 353 are formed with a plurality of small projections shaped so as to correspond to the small compressed spots 20 as shown by FIG. 1. Each of the projections 351 is necessary and sufficient to form all compressed lines included in the individual liner 10 and, from the viewpoint of this, each of the projections 351 can be referred to as "compressing unit". These projections 351 formed on the peripheral surface of the first roll 302a are arranged in five rows each extending to the machine direction MD wherein the first row includes the projections 351a, 351b and 351c; the second row includes the projections 351d, 351e and 351f; the third row includes the projections 351g, 351h and 351i; the fourth row includes the projections 351j, 351k and 351l; and the fifth row includes the projections 351m, 351n and 351o. These projections 351a through 351o referred to herein generically as the projection 351 are same in shape as well as in size and respectively include in addition to lateral projection segments 341, 342 having planar shapes corresponding to the compressed intermediate segments 21e, 22e in the first and second compressed lines 21, 22, end region projection segments 343, 344 extending between the lateral projection segments 341, 342 and adapted to form the compressed end segments 21c, 21d, 22c, 22d in the respective end regions 31, 32. In each of the five rows, each pair of projections 351 being adjacent in the machine direction MD may be spaced from each other by a dimension X. In each pair of the rows being adjacent in the cross direction CD, for example, in the first and second rows, the end region projection segment 343 of the projection 351d and the end region projection segment 344 of the projection 351e in the second row are positioned adjacent the lateral projection segment 342 of the projection 351a in the first row as viewed in the cross direction CD. In this manner, there is an offset between the projection 351 of the first row and the projection 351 of the second row and the offset is in the length of approximately by a half of the length of the projection 351. As explained, the first row includes the projections 351a-351c as the projection 351 and the second row includes the projection 351d-351f as the projection 351. The end region projection segment 343 of the projection 351d is opposed to the end region projection segment 344 of the projection 351e in the machine direction MD. On such first roll 302a, the lateral projection segment 342 of the projection 351a in the first row, the end region projection segment 343 of the projection 351d and the end region projection segment 344 of the projection 351e surround a region 360 in which the small projection 352 is formed. Such small projection 352 has the same height as that of the projection 351. Referring to FIG. 3, the second laminated web 115 fed to the paired compression rolls 302 is indicated by imaginary lines.

Figure 5:
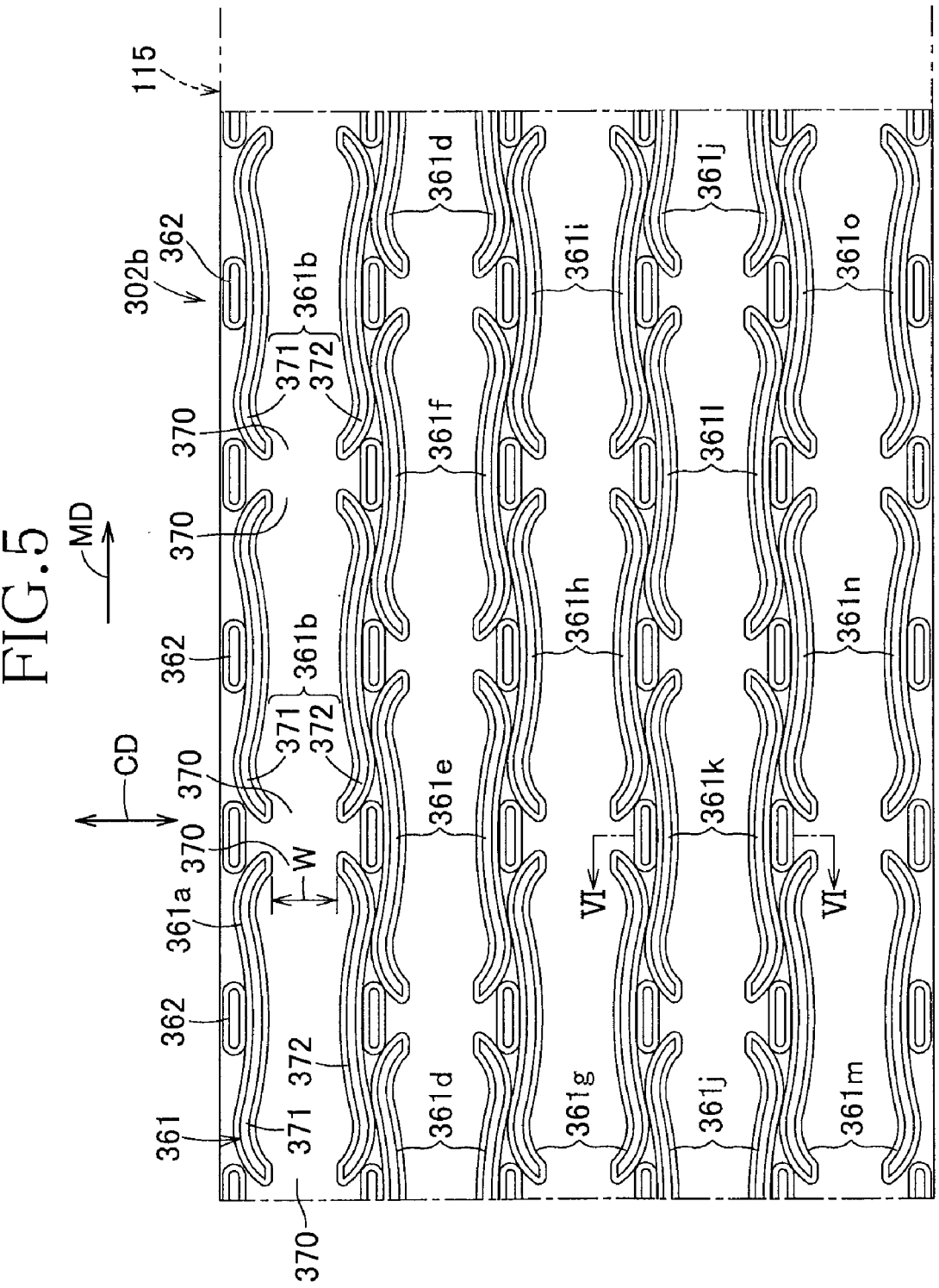
FIG. 5 illustrates the peripheral surface of the second roll constituting the paired compression rolls as has been flatly developed.
Figure 6:
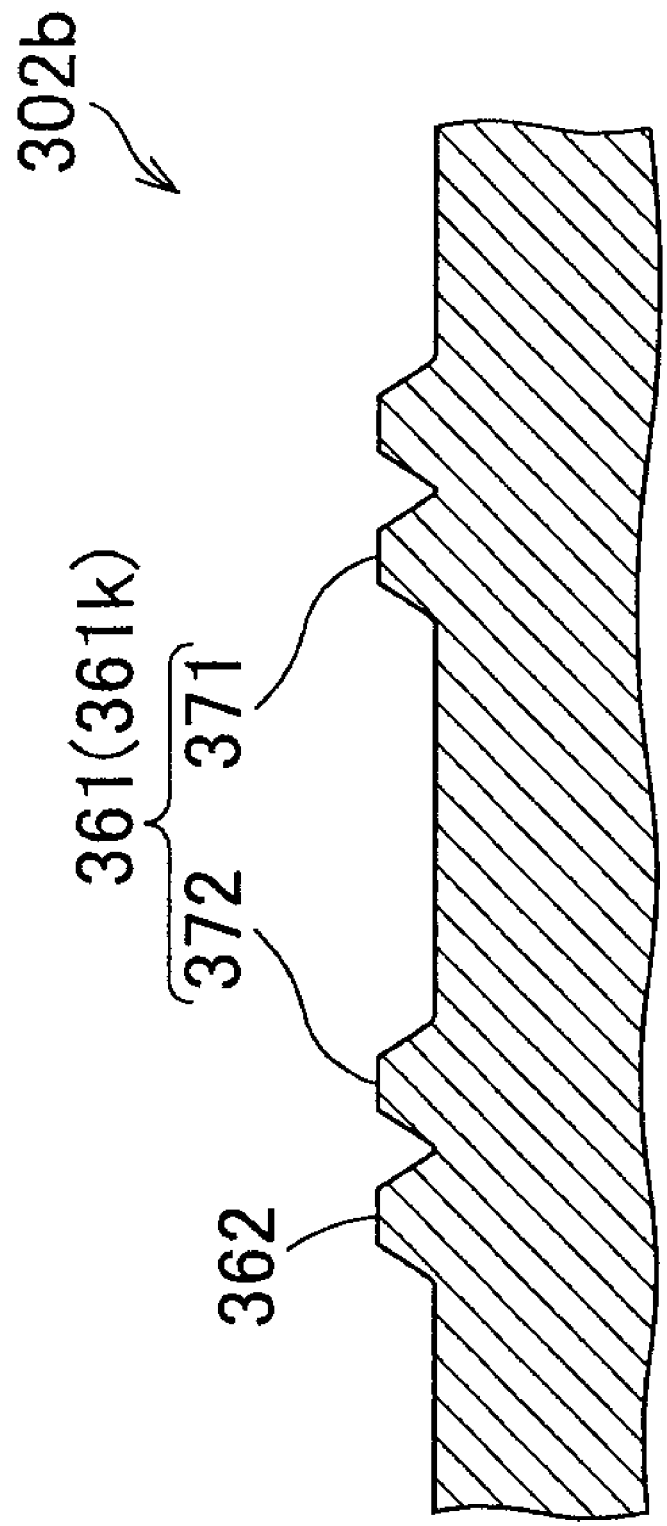
FIG. 6 is a sectional view taken along a line VI-VI in FIG. 5.

FIG. 5 illustrates the peripheral surface of the second roll 302b constituting the paired compression rolls 302 as has been flatly developed and FIG. 6 is a sectional view taken along a line VI-VI in FIG. 5. Referring to FIG. 5, the second laminated web 115 is indicated by imaginary lines. The second roll 302b provides anvils adapted to cooperate with the associated projections 351 on the first roll 302a and, more specifically, the second roll 302b is formed on its peripheral surface with anvil-mode projections 361 opposed to the associated projections 351 by the intermediary with the second laminated web 115 and anvil-mode small projections 362 opposed to the associated small projections 352. It should be appreciated that each of the anvil-mode projections 361 comprises an anvil-mode first projection 371 and an anvil-mode second projection 372 spaced from and opposite to each other in the cross direction CD. The anvil-mode first projection 371 cooperates with the associated projection 351 to form the first compressed line 21 in the liner 10 and has a same planar shape as the first compressed line 21. The anvil-mode second projection 372 cooperates with the associated projection 351 to form the second compressed line 22 in the liner 10 and has a same planar shape as the second compressed line 22. The second roll 302b is provided with a region 370 between respective ends of these anvil-mode first and second projections spaced from each other in the cross direction CD by a dimension W and this region 370 leaves a non-compressed region in the second laminated web 115. These anvil-mode projections 361 are compressing units adapted to complement the associated projections 351. These anvil-mode projections 361 are arranged in the machine direction MD to form rows wherein a first row includes the anvil-mode projections 361a, 361b and 361c, a second row includes the anvil-mode projections 361d, 361e and 361f, a third row includes the anvil-mode projections 361g, 361h and 361i, a fourth row includes the anvil-mode projections 361j, 361k and 361l, and fifth row includes the anvil-mode projections 361m, 361n and 361o. The anvil-mode projections 361 in these five rows cooperate with the associated projections 351 in the five rows to form the second laminated web 115 with the first and second compressed lines 21, 22. The anvil-mode small projections 362 cooperate with the associated small projections 352 to compress the second laminated web 115.

With the paired compression rolls 302 designed as has been described above, the liners 10 can be obtained in a plurality of rows at once and, in the respective rows, the liners 10 can be obtained intermittently in the machine direction MD. On the first roll 302a, the end region projection segment 343 of the projection 351d and the end region projection segment 344 of the projection 351e both describing convexly curved lines in the second row are positioned closely to, as viewed in the cross direction CD, the concavely curved line describing lateral projection segment 342 of the projection 351a in the first row. Such arrangement allows a given area of the second laminated web 115 to be used to make the liners 10 as efficiently as possible and thereby allows scrap inevitably generated when the liners 10 are cut out from the second laminated web 115 to be reduced. In contrast with the arrangement of the projections 351 and the anvil-mode projections 361 as illustrated by FIGS. 3 and 5, it is assumed that these projections 351 and anvil-mode projections 361 of the respective rows are aligned in the cross direction CD. In this case, between each pair of the concavely curved line describing lateral compression segments 341, 342 being adjacent and opposed to each other in the cross direction CD would leave therebetween a relatively large area as scrap which will be generated after the liners 10 have been cut out from the second laminated web 115.

In the paired compression rolls 302, the regions used to compress the bodily fluid absorbent web 115 comprise the projections 351 formed on the peripheral surface of the first roll 302a and the anvil-mode projections 361 formed on the peripheral surface of the second roll 302b. Consequentially, the first and second rolls 302a, 302b are sufficiently spaced from each other in regions defined around these projections 351, 361 to assure that the web can move into these regions around the respective projections 351, 361 in the machine direction MD as well as in the cross direction CD during the step of compression. In this way, the first compressed line 21 and the second compressed line 22 can be neatly formed.

With the paired compression rolls 302 as illustrated by FIGS. 3 through 6, the presence of the small projections 352 and the anvil-mode small projections 362 provide another advantageous effect. More specifically, these small projections 352 and anvil-mode small projections 362 also anticipate to compress the second laminated web 115 and, in consequence, an area over which the first roll 302a and the second roll 302b come in contact with the second laminated web 115 is not be abruptly changed. In this way, possibility that the second laminated web 115 and the first and second rolls 302a, 302b might be damaged can be significantly decreased in comparison with the case in which the paired compression rolls 302 is formed with neither the small projections 352 nor the anvil-mode small projections 362. Furthermore, the first roll 302a is formed with the small projections 352 not only at opposite ends in the axial direction but also between each pair of the adjacent rows of the projections 351. In a similar way, the second roll 302b is formed with the anvil-mode small projections 362 not only at opposite ends in the axial direction but also between each pair of the adjacent rows of the anvil-mode projections 361. With this unique arrangement, the bodily fluid absorbent web 115 can be evenly compressed not only at the transversely opposite side regions thereof but also at the intermediate region thereof in the step of compressing the web 115 and thereby it is possible to restrict the bodily fluid absorbent web over its full width from undesirable displacement in the machine direction MD as well as in the cross direction CD. It is thus easy for the first and second rolls 302a, 302b to prevent compression of the web 115 from being biased in the cross direction CD.

Figure 7:
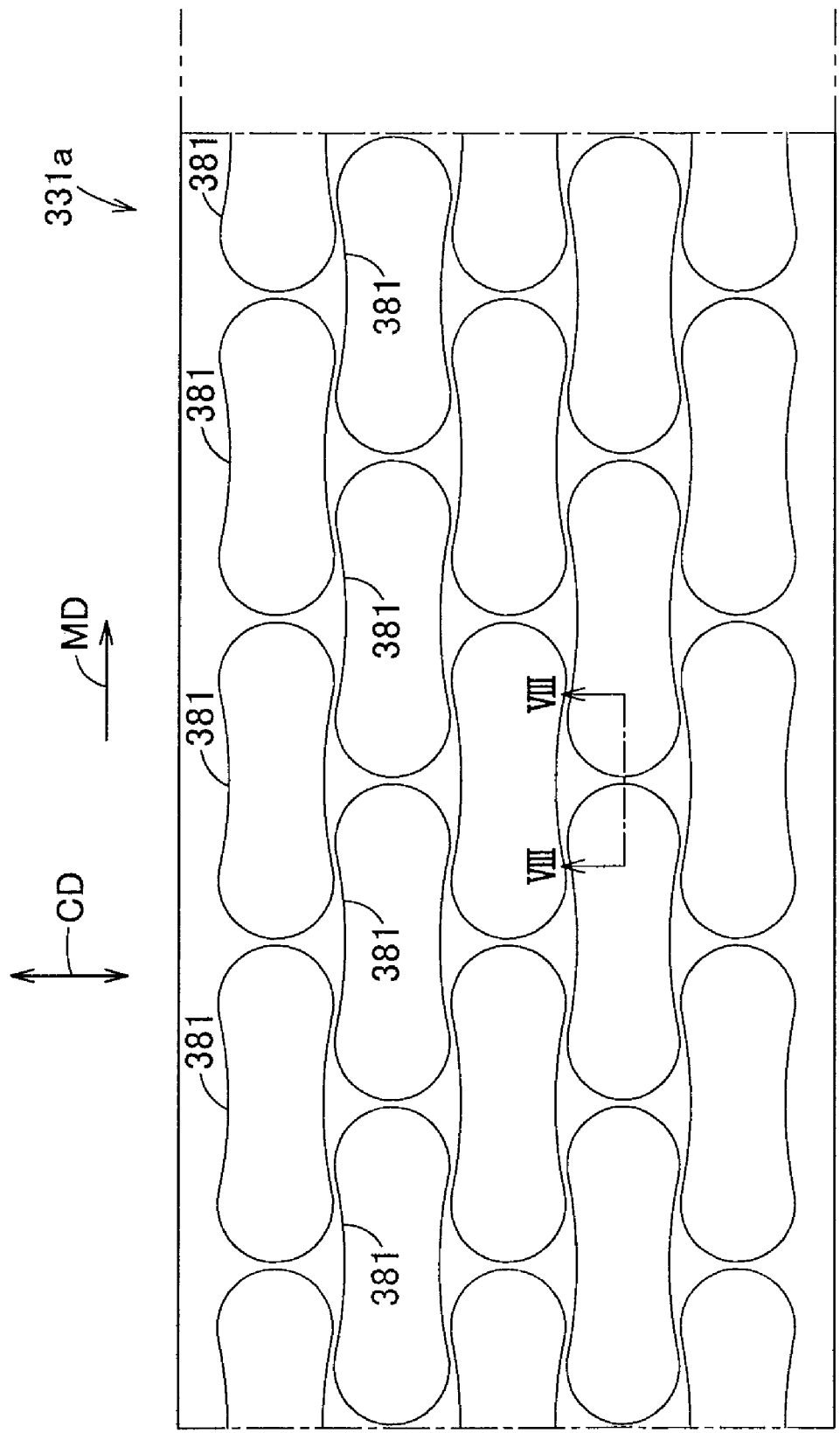
FIG. 7 illustrates the second cutter roll as has been flatly developed.
Figure 8:
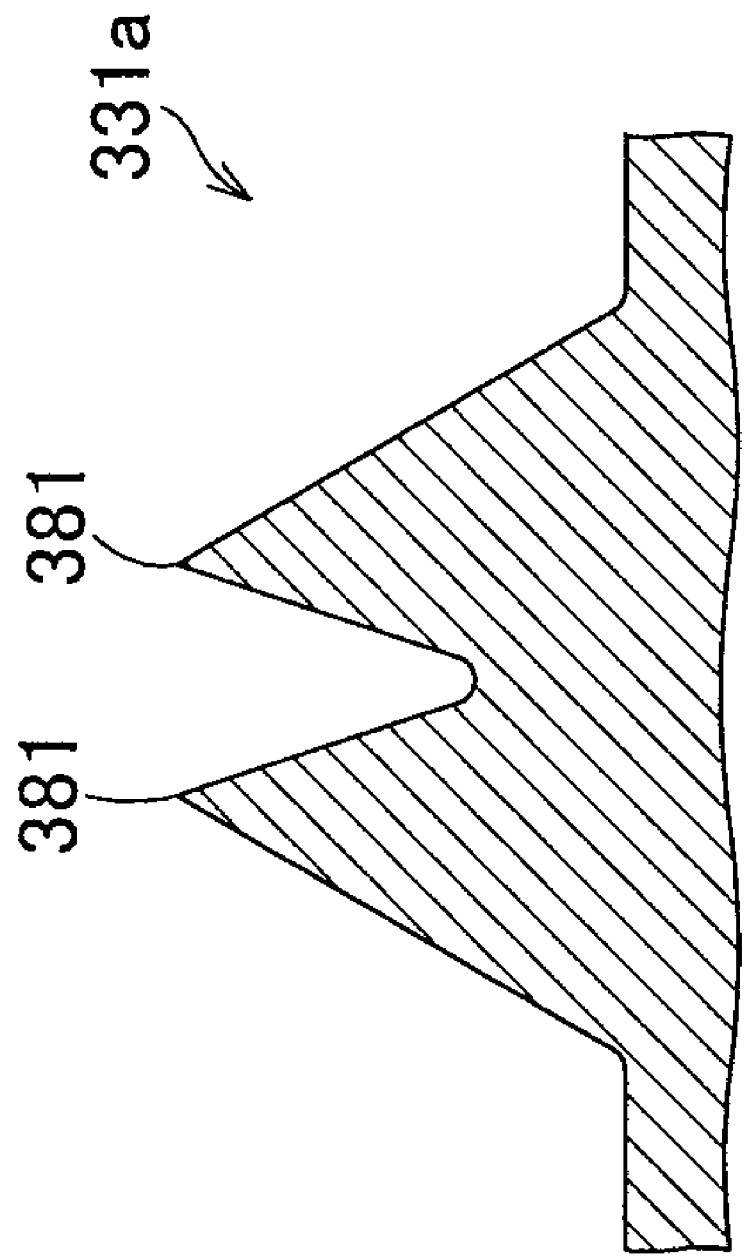
FIG. 8 is a sectional view taken along a line VIII-VIII in FIG. 7.

FIG. 7 illustrates the first cutter roll 331a constituting the paired cutter rolls 330 illustrated by FIG. 2 as has been flatly developed and FIG. 8 is a sectional view taken along a line VIII-VIII in FIG. 7. Referring to FIG. 7, the first cutter roll 331a is formed on its peripheral surface with a plurality of oval knife edges 381 each having a shape conforming to the contour shape of the liner 10 shown by FIG. 1. The knife edges 381 are arranged in the machine direction MD at the same pitch as the pitch at which the projections 351 are arranged in the machine direction MD on the first compression roll 302a so that a plurality of rows of the knife edges 381 may be formed. In each pair of the rows being adjacent in the cross direction CD, there is an offset between the one row having the knife edges 381 arranged in the machine direction MD and the other row having the knife edges 381 arranged in the machine direction MD and the offset is in the length of approximately by a half of the inner diameter of the individual knife edge 281 as measured in the machine direction MD. The second cutter roll 331b cooperating with such first cutter roll 331a has a smooth peripheral surface.

Figure 9:
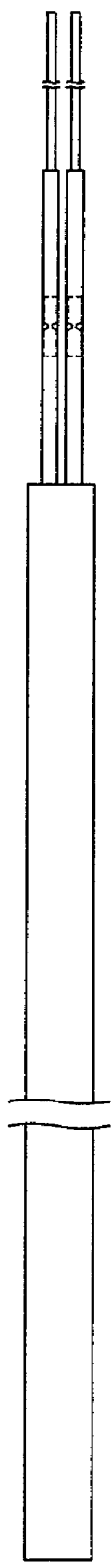
FIG. 9 is a side view of the heater.

FIG. 9 is a side view of a rod heater 380 adapted to be inserted into shaft(s) of the first roll 302a and/or the second roll 302b of the paired compression rolls 302 and thereby to control a surface temperature of the projections 351 and/or the anvil-mode projections 361 at a desired temperature level. The rod heater 380 is used to maintain the peripheral surface of the roll incorporated with the rod heater 380 at an even temperature in the axial direction and thereby to assure two or more liners 10 arranged in the cross direction CD to have the first and second lateral compressed segments 21, 22 formed under a same condition of the temperature. To fulfill such function, the rod heater 380 is designed to have a watt density higher at longitudinally opposite end regions than in a longitudinally intermediate region. Specifically, taking account of a fact that the first roll 302a and/or the second roll 302b may typically have heat loss higher in the axially opposite end region than in the axially intermediate region, the watt density distribution of the rod heater 380 in the longitudinal direction thereof is previously adjusted in order to compensate the heat loss. When the first and second compressed lines 21, 22 are used as attaching means, as will be described later, to attach a pair of liners in a detachable manner and thereby to form a composite liner 390 (See FIG. 11), use of the rod heater 380 as illustrated by FIG. 9 will be essential since it is important to assure that the first and second compressed lines 21, 22 for each of the liners 10 are properly formed.

Figure 10:
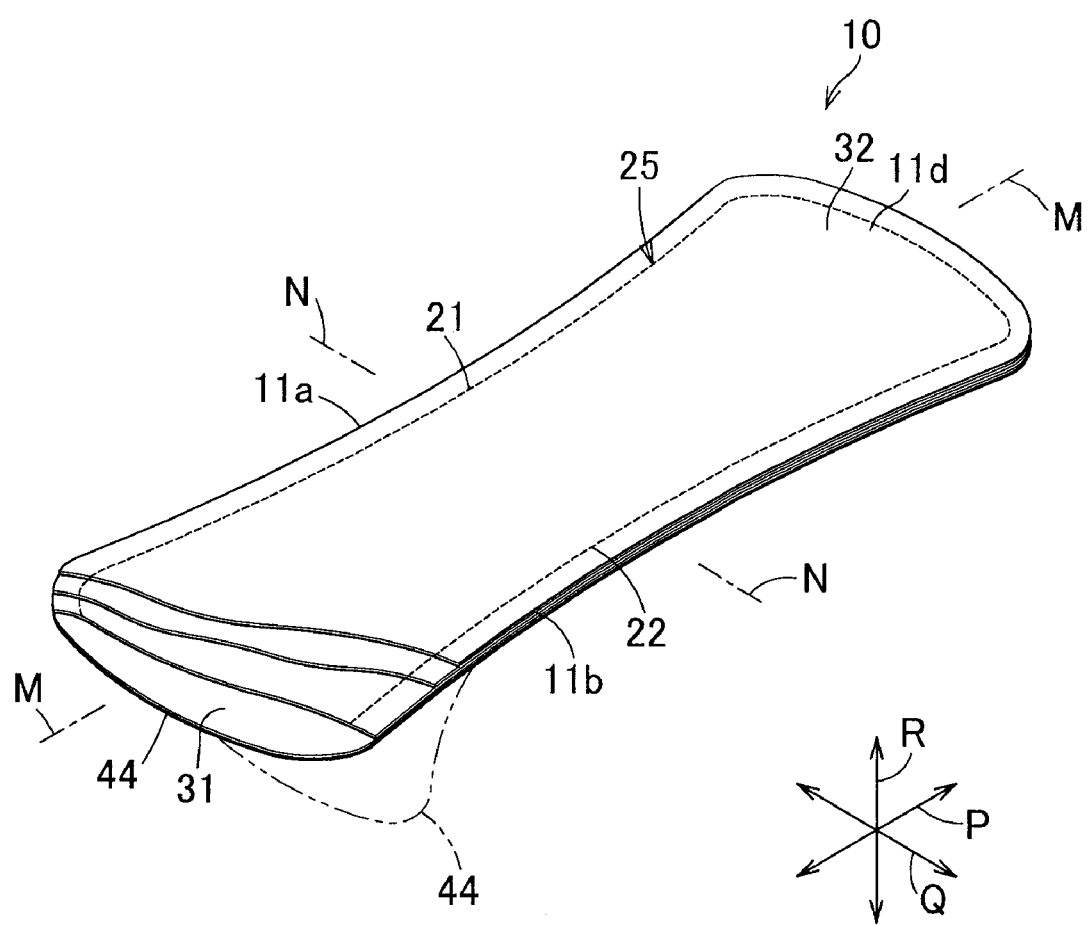
FIG. 10 is a view similar to FIG. 1, showing another embodiment of the liner.

FIG. 10 is a view similar to FIG. 1, showing another embodiment of the liner 10 which may be made by the method and the apparatus according to the present invention. In the case of the liner 10 shown by FIG. 10, the first and second compressed lines 21, 22 formed along the side edges 11a, 11b of the liner 10 are connected to each other in the end regions 31, 32 of the liner 10 so as to describe a loop-shaped compressed line 25. To obtain such loop-shaped compressed line 25, the second roll 302b constituting the paired compression rolls 302 formed with the anvil-mode first projections 371 and the anvil-mode second projections 372 as exemplarily illustrated by FIG. 5 may be replaced by a second roll 302b formed with a loop-shaped anvil-mode projections corresponding to the compressed loop-shaped line 25 or replaced by the second roll 302b having a smooth peripheral surface.

Figure 11:
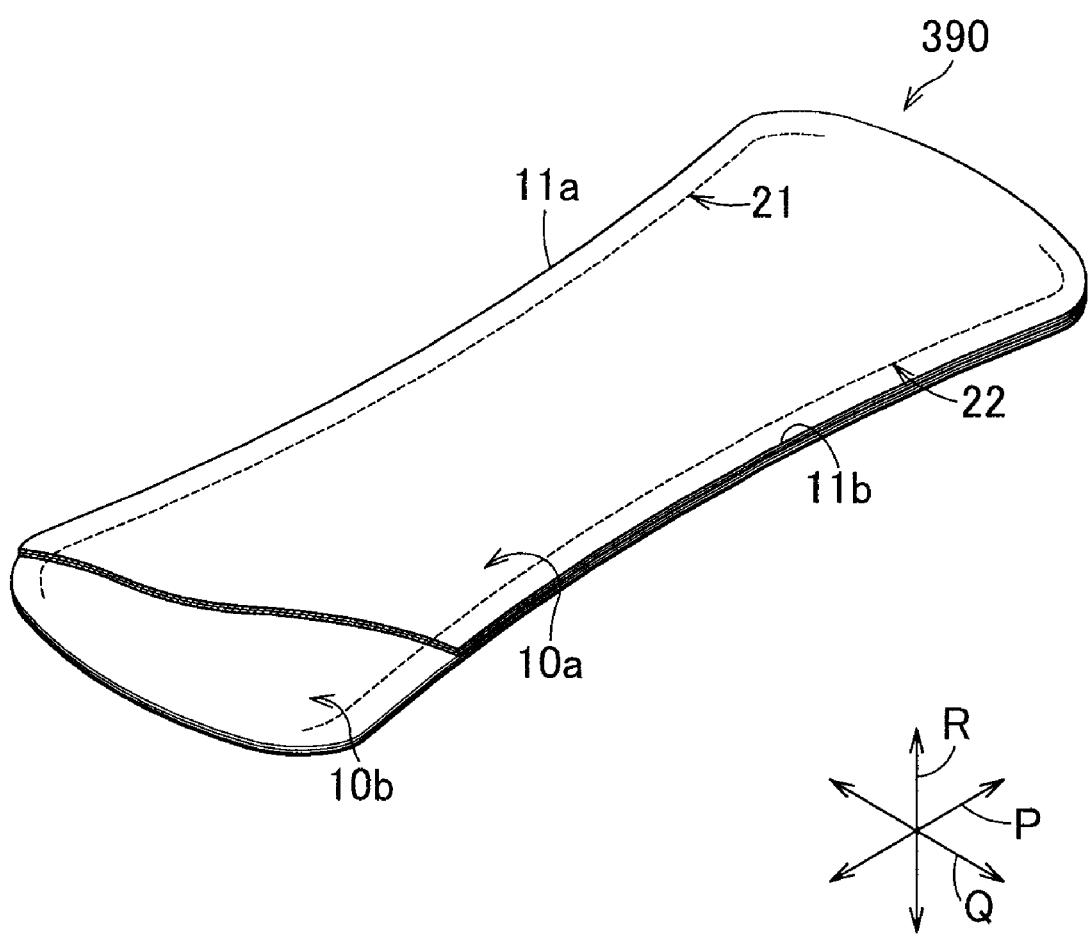
FIG. 11 is a view similar to FIG. 1, showing a still another embodiment of the liner.

FIG. 11 also is a view similar to FIG. 1, showing a still another embodiment of the liner which can be made by the method and the apparatus according to the present invention. The liner shown by FIG. 11 is the composite liner 390 comprising an upper liner 10a and a lower liner 10b seperably attached together wherein both the upper liner 10a and the lower liner 10b may be same as the liner 10 as shown by FIG. 1. However, it should be appreciated that fibrous material (not shown) forming the upper liner 10a is forced into the lower liner 10b along the first compressed line 21 and the second compressed line 22 formed in the upper liner 10a and mechanically entangled with fibrous material (not shown) forming the lower liner 10b. Such composite liner 390 may be obtained by, in the process schematically illustrated by FIG. 2, placing a laminated web 113 indicated by the imaginary lines upon the second laminated web 115 and then feeding these two webs 113, 115 so as to pass through the paired compression rolls 302 in the machine direction MD. It should be appreciated here that the laminated web 113 is bodily fluid absorbent web provided on its side facing the second laminated web 115 with bodily fluid impervious web formed, e.g., by plastic film. In the paired compression rolls 302 used for this embodiment, height, pressure and temperature of the projections 351 and the small projections 352 formed on the first roll 302a should be adjusted so that the small compressed spots 20 may extend through the laminated web 113 into the second laminated web 115. In the individual composite liner 390, peel strength of the upper liner 10a along the first and second compressed lines 21, 22 should be substantially of the same degree. Also with respect to a plurality of the composite liners 390 obtained simultaneously in a plurality of rows in the process schematically illustrated by FIG. 2, the peel strength of the respective composite liners 10a should be substantially of the same degree. Such requirements are easily met by using the exemplarily illustrated paired compression rolls 302 according to the present invention since such roll pair facilitates the bodily fluid absorbent web 115 to be evenly compressed over the full width thereof and thereby assures the peel strength of the upper liners 10a of the respective composite liners 390 to be stabilized and to be uniform.

The invention claimed is:

1. A method of making a bodily fluid absorbent pad, said pad having a longitudinal direction, a transverse direction and a thickness direction being orthogonal one to another and elongated in said longitudinal direction,
   wherein said pad having
      a skin-contact surface and a skin-noncontact surface opposite to said skin-contact surface as viewed in said thickness direction,
      side edges extending in said longitudinal direction,
      first and second end regions opposite to each other in said longitudinal direction, and
      an intermediate region extending between said first and second end regions, a dimension of said pad in the transverse direction in the first and second end regions being larger than that in the intermediate region, and
   wherein said pad on said skin-contact surface includes compressed lines extending in said longitudinal direction inboard of the respective side edges, said method comprising the steps of:
   feeding a bodily fluid absorbent web in a machine direction; and
   compressing said bodily fluid absorbent web between a pair of compression rolls to form said compressed lines including first and second compressed segments in said first and second end regions, respectively, and third compressed segments in said intermediate region,
   wherein at least one of the compression rolls includes compressing units, which project from a peripheral surface of the compression roll,
   wherein the compressing units are arranged in at least two rows adjacent to each other and extending in the machine direction,
   wherein at least one of the compression rolls further includes projections projecting from the peripheral surface of said at least one of the compression rolls and extending in the machine direction along said rows of the compressing units, and
   wherein one row of the compressing units is offset from the other row of said compressing units in the machine direction so that said first and second compressed segments formed by one row of said compressing units are lateral to said third compressed segment formed by the other row of said compressing units in a cross direction substantially perpendicular to the machine direction, respectively.

2. The method according to claim 1, further comprising the step of:
cutting the bodily fluid absorbent web through a pair of cutter rolls provided downstream of said paired compression rolls in said machine direction to cut the bodily fluid absorbent pads from said bodily fluid absorbent web,
wherein one of the cutter rolls includes knife edges on a peripheral surface thereof and corresponding to said compressing units of said compression rolls in said machine direction as well as in said cross direction.

3. The method according to claim 1, further comprising: between said step of compressing and said step of cutting,
the step of permanently attaching a bodily fluid impervious web defining said skin-noncontact surface in said bodily fluid absorbent pad to said bodily fluid absorbent web.

4. The method according to claim 1, further comprising: before said step of compressing, the steps of
placing another bodily fluid absorbent web upon a surface of said bodily fluid absorbent web defining said skin-contact surface of said bodily fluid absorbent pad, and then
attaching said bodily fluid absorbent webs to each other to form a bodily fluid absorbent composite web defining said bodily fluid absorbent pads.

5. The method according to claim 1, wherein the step of compressing comprises heating said bodily fluid absorbent web between the pair of compression rolls,
wherein at least one of the said compression rolls includes a rod heater inserted thereinto,
wherein said rod heater has a watt density higher at end regions thereof, which are opposite to each other in the cross direction, than in an intermediate region between said end regions.

6. The method according to claim 1, wherein both the compression rolls have the compressing units arranged on the respective peripheral surfaces thereof, and
in the step of compressing, the compressing units of one of the compression rolls engage the corresponding compressing units of the other compression roll to form the compressed lines.

7. The method according to claim 1, wherein both the compression rolls have the projections arranged on the respective peripheral surfaces thereof, and
in the step of compressing, the projections of one of the compression rolls engage the corresponding projections of the other compression roll to form the compressed lines.

8. The method according to claim 1, wherein said projections are arranged in at least two rows extending in the machine direction and alternatingly arranged with said at least two rows of the compressing units in the cross direction.

9. The method according to claim 8, wherein said at least two rows of the compressing units are parallel to each other, and said at least two rows of the projections are parallel to each other.

10. The method according to claim 1, wherein
each of the compressing units includes, in the machine direction, opposite end portions and an intermediate portion between the end portions, and
in the cross direction, the projections are adjacent to the intermediate portions of the compressing units in one row and adjacent to the end portions of the compressing units in the other row.

11. The method according to claim 1, wherein two adjacent compressing units in each row of the compressing units are spaced away from each other in the machine direction.

12. The method according to claim 1, wherein each of the compressing units in one of the compression rolls has a closed shape, and each of the compressing units in the other compression roll has a non-closed shape.

13. The method according to claim 1, wherein each of the projections has first and second sections spaced away from each other in the cross direction to define a non-compressed portion at the end regions of the bodily fluid absorbent pads.

14. The method according to claim 1, wherein each of the compressing units and the projections has a top surface such that the compressed lines are intermittently formed in the step of compressing.

15. The method according to claim 2, wherein one of the cutter rolls has said knife edges and the other cutter roll has a smooth peripheral surface.

16. The method according to claim 1, wherein the step of compressing comprises forming an additional compressed line in said bodily fluid absorbent web between the projections but not in said bodily fluid absorbent pad.

* * * * *